US00PP16812P2

(12) United States Plant Patent
Bulk

(10) Patent No.: US PP16,812 P2
(45) Date of Patent: Jul. 11, 2006

(54) ***HYDRANGEA* PLANT NAMED 'BULK'**

(50) Latin Name: *Hydrangea paniculata*
Varietal Denomination: Bulk

(75) Inventor: Rein Bulk, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 20 days.

(21) Appl. No.: 11/097,692

(22) Filed: Mar. 31, 2005

(51) Int. Cl.
*A01H 5/00* (2006.01)

(52) U.S. Cl. ..... Plt./250
(58) Field of Classification Search ..... Plt./250
See application file for complete search history.

(56) References Cited

PUBLICATIONS

UPOV–ROM GTITM, Plant Variety Database, 2005/03 GTI Jouive Retrieval Software, Citation for *Hydrangea* 'Bulk'.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Hydrangea* plant named 'Bulk', characterized by its upright and somewhat outwardly spreading plant habit; uniform and even growth habit; early and freely flowering habit; large upright flower panicles; and large panicles with white-colored sterile flowers that become red purple in color in the late summer and fall.

2 Drawing Sheets

Botanical designation: *Hydrangea paniculata.*
Cultivar denomination: 'Bulk'.

BACKGROUND OF THE INVENTION

The present Invention relates to a new and distinct cultivar of *Hydrangea* plant, botanically known as *Hydrangea paniculata,* and hereinafter referred to by the cultivar name Bulk.

The new *Hydrangea* is a chance seedling from an open-pollination of two unknown *Hydrangea paniculata* selections. The cultivar Bulk was discovered and selected by the Inventor as a single plant within the progeny of the stated open-pollination in a controlled environment in Boskoop, The Netherlands in 1991.

Asexual reproduction of the new cultivar by softwood cuttings in Boskoop, The Netherlands since the summer of 2002, has shown that the unique features of this new *Hydrangea* are stable and reproduced true to type in successive generations.

SUMMARY OF THE INVENTION

Plants of the cultivar Bulk have not been observed under all possible environmental conditions. The phenotype may vary somewhat with variations in environment such as temperature and light intensity without, however, any variance in genotype.

The following traits have been repeatedly observed and are determined to be the unique characteristics of 'Bulk'. These characteristics in combination distinguish 'Bulk' as a new and distinct cultivar:

1. Upright and somewhat outwardly spreading plant habit.
2. Uniform and even growth habit.
3. Early and freely flowering habit.
4. Large upright flower panicles.

5. Large panicles with white-colored sterile flowers that become red purple in color in the late summer and fall.

Plants of the new *Hydrangea* can be compared to plants of the *Hydrangea* cultivar Pink Diamond, not patented. In side-by-side comparisons conducted in Grand Haven, Mich., plants of the new *Hydrangea* differed from plants of the cultivar Pink Diamond in the following characteristics:

1. Plants of the new *Hydrangea* were smaller than plants of the cultivar Pink Diamond.
2. Plants of the new *Hydrangea* were much more freely branching than plants of the cultivar Pink Diamond.
3. Plants of the new *Hydrangea* had longer leaves than plants of the cultivar Pink Diamond.
4. Plants of the new *Hydrangea* started flowering earlier than plants of the cultivar Pink Diamond.
5. Plants of the new *Hydrangea* had fewer sterile flowers per inflorescence than plants of the cultivar Pink Diamond.
6. Plants of the new *Hydrangea* had longer lasting flowers sterile flowers than plants of the cultivar Pink Diamond.
7. Plants of the new *Hydrangea* and the cultivar Pink Diamond differed in flower coloration in the late summer and fall as flowers of plants of the new *Hydrangea* were darker in color than flowers of the cultivar Pink Diamond.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph on the first sheet is a side perspective view of a typical plant of the new *Hydrangea* in the summer.

The photograph at the bottom of the second sheet is a side perspective view of a typical plant of 'Bulk' in August showing the red purple coloration that develops during the late summer and fall.

The photograph at the top of the second sheet comprises a close-up view of a typical inflorescence of 'Bulk' showing the red purple coloration that develops during the late summer and fall.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in ground beds in an outdoor nursery and under conditions which closely approximate commercial production conditions. During the production of the plants, day temperatures ranged from 20 to 30° C. and night temperatures ranged from 12 to 20° C. Plants were about two years old when the photographs and description were taken. Photographs and description were taken during the summer and fall.

Botanical classification: *Hydrangea paniculata* cultivar Bulk.

Parentage:

*Female, or seed, parent.*—Unknown *Hydrangea paniculata* selection, not patented.

*Male, or pollen, parent.*—Unknown *Hydrangea paniculata* selection, not patented.

Propagation:

*Type cutting.*—By softwood cuttings.

*Time to initiate roots.*—About 20 days at 20° C.

*Time to produce a rooted cutting or liner.*—About two months at 20° C.

*Root description.*—Thick; creamy white in color.

*Rooting habit.*—Freely branching; dense.

Plant description:

*Form/growth habit.*—Upright and somewhat outwardly spreading plant habit; inverted triangle; dense and bushy perennial shrub; uniform, even and vigorous growth habit.

*Plant height, soil level to top of plant plane.*—About 75 cm.

*Plant diameter or area of spread.*—About 75 cm.

*Branching habit.*—Freely branching, about 52 lateral branches per plant. Pruning will enhance branching potential.

*Lateral branches.*—Length: About 78 cm. Diameter: About 7 mm. Internode length: About 8.5 cm. Strength: Very strong. Texture: Smooth, glabrous. Color: 175B.

*Foliage description.*—Arrangement: Opposite, simple. Length: About 15.3 cm. Width: About 7.5 cm. Shape: Ovate. Apex: Acute. Base: Obtuse. Margin: Serrulate. Texture, upper and lower surfaces: Slightly pubescent; rugose. Venation pattern: Pinnate. Color: Developing and fully expanded foliage, upper surface: 146A. Developing and fully expanded foliage, lower surface: 146D. Venation, upper and lower surfaces: 147D. Petiole: Length: About 2.5 cm. Diameter: About 3 mm. Texture, upper and lower surfaces: Smooth, glabrous. Color, upper and lower surfaces: 187C.

Flower description:

*Flower type and habit.*—Single fertile and sterile flowers arranged on large terminal panicles. Sterile flowers with large showy sepals, but without petals and reproductive organs. Fertile flowers, inconspicuous, but with petals, sepals and reproductive organs. Sterile flowers persistent; fertile flowers not persistent. Fertile and sterile flowers are not fragrant.

*Natural flowering season.*—Early flowering habit and long flowering period; flowering from late May until late October in Grand Haven, Mich.

*Flower longevity.*—Long-lasting flowers; sterile flowers last about 24 weeks on the plant. As cut flowering stems, panicles last about four weeks.

*Quantity of flowers.*—Freely flowering habit; one terminal panicle per lateral branch with about 24 sterile flowers and about 382 fertile flowers per panicle.

*Panicle height.*—About 16 cm.

*Panicle diameter.*—About 15 cm.

*Panicle shape.*—Conical.

*Flower diameter.*—Sterile flowers: About 4.9 cm. Fertile flowers: About 9 mm.

*Flower depth (height).*—Sterile flowers: About 1.1 cm. Fertile flowers: About 9 mm.

*Flower buds, fertile and sterile flowers.*—Length: About 4 mm. Diameter: About 3 mm. Shape: Elliptic to oval. Color: Close to 155A.

*Petals (petals present only on fertile flowers; sterile flowers do not have petals).*—Arrangement: About five. Length: About 3 mm. Width: About 2 mm. Shape: Lanceolate. Apex: Acute. Base: Obtuse. Margin: Entire. Texture, upper and lower surfaces: Smooth, glabrous. Color: When opening, upper and lower surfaces: 155D. Fully opened, upper and lower surfaces: 155D.

*Sepals.*—Quantity per flower: Fertile flowers: About five, fused into a calyx. Sterile flowers: About four. Length: Fertile flowers: Less than 1 mm. Sterile flowers: About 2.4 cm. Width: Fertile flowers: Less than 1 mm. Sterile flowers: About 2.4 cm. Shape: Fertile flowers: Connate. Sterile flowers: Obovate; rounded. Apex: Fertile flowers: Acute. Sterile flowers: Obtuse to retuse. Base: Fertile flowers: Fused. Sterile flowers: Cuneate. Margin, fertile and sterile flowers: Entire. Texture, fertile and sterile flowers, upper and lower surfaces: Smooth, glabrous. Color: Fertile flowers: When opening and fully opened, upper and lower surfaces, 155A. Sterile flowers: When opening, upper and lower surfaces: 155D. Fully opened, upper and lower surfaces: 155D; color becoming closer to 66A with development towards the end of summer and early fall.

*Peduncles.*—Angle: Mostly erect. Strength: Strong. Length: About 13.3 cm. Diameter: About 5 mm. Texture: Smooth. Color: 147D.

*Pedicels.*—Angle, fertile and sterile flowers: Variable, dependent on position in the panicle; erect to about 90° from vertical. Strength, fertile and sterile flowers: Strong. Length: Fertile flowers: About 3 mm. Sterile flowers: About 2.7 cm. Diameter: Fertile flowers: About 1 mm. Sterile flowers: About 1.5 mm. Texture, fertile and sterile flowers: Smooth. Color, fertile and sterile flowers: 155A.

*Reproductive organs (reproductive organs present only on fertile flowers; sterile flowers do not have repro-*

*ductive organs*).—Stamens: Quantity per flower: About ten. Anther shape: Round. Anther length: About 1 mm. Anther color: 155A. Pollen amount: Scarce. Pollen color: 155A. Pistils: Pistil quantity per flower: Three, fused. Pistil length: About 4 mm. Stigma shape: Oval. Stigma color: 155A. Style length: About 1 mm. Style color: 155A. Ovary color: 155A.

*Fruit.*—Type: Capsule, dehiscent. Length: About 5 mm. Diameter: About 3 mm. Shape: Urn-shaped. Color: Close to 177A.

*Seed.*—Minute, dust-like. Length: Less than 0.5 mm. Diameter: Less than 0.5 mm. Color: Brown.

Disease/pest resistance: Under commercial production conditions, plants of the new *Hydrangea* have not been observed to be resistant to pathogens or pests common to *Hydrangea*.

Weather tolerance: Plants of the new *Hydrangea* have been shown to be tolerant to temperatures ranging from −35 to 38° C. Flowers of plants of the new *Hydrangea* relatively tolerant to wind and rain.

It is claimed:

1. A new and distinct cultivar of *Hydrangea* plant named 'Bulk', as illustrated and described.

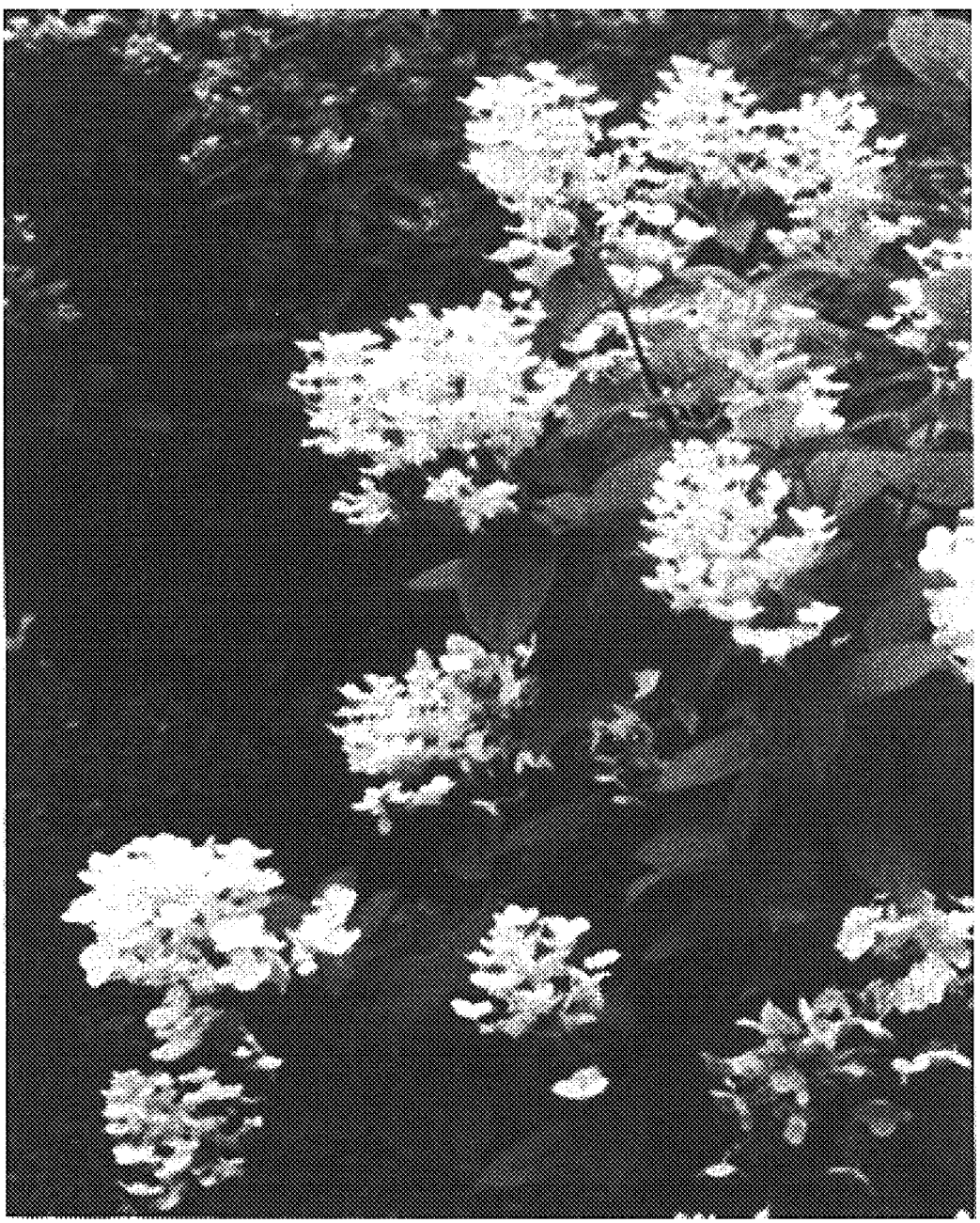

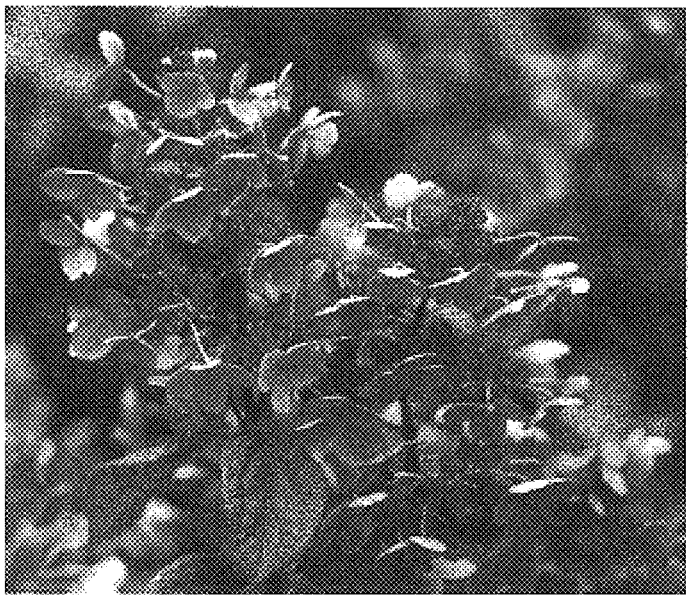
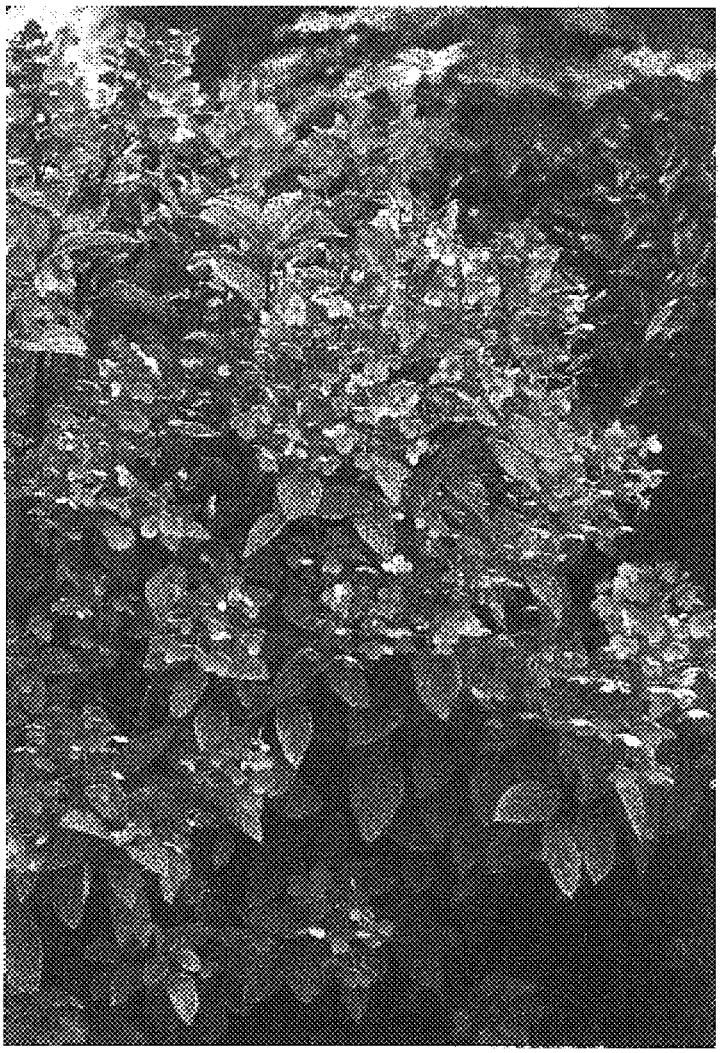

* * * * *